United States Patent
Yarbrough

(10) Patent No.: US 10,561,626 B2
(45) Date of Patent: *Feb. 18, 2020

(54) METHOD FOR TREATING URUSHIOL INDUCED CONTACT DERMATITIS

(75) Inventor: William M. Yarbrough, Peoria, IL (US)

(73) Assignee: The William M. Yarbrough Foundation, Peoria, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/175,917

(22) Filed: Jul. 6, 2005

(65) Prior Publication Data

US 2006/0147405 A1 Jul. 6, 2006

Related U.S. Application Data

(63) Continuation of application No. 10/200,691, filed on Jul. 22, 2002, now Pat. No. 7,008,963, which is a continuation-in-part of application No. 09/347,714, filed on Jul. 3, 1999, now Pat. No. 6,423,746.

(51) Int. Cl.
  *A61K 31/185* (2006.01)
  *A61K 31/05* (2006.01)
  *A61K 31/195* (2006.01)
  *A61K 31/20* (2006.01)

(52) U.S. Cl.
  CPC ............ *A61K 31/185* (2013.01); *A61K 31/05* (2013.01); *A61K 31/195* (2013.01); *A61K 31/20* (2013.01); *Y10S 514/862* (2013.01)

(58) Field of Classification Search
  CPC .. A61K 2300/00; A61K 31/195; A61K 31/20; A61K 31/05; A61K 31/185; Y10S 514/862
  See application file for complete search history.

(56) References Cited

U.S. PATENT DOCUMENTS 5,753,245 A * 5/1998 Fowler .................... A61Q 5/02
424/401

OTHER PUBLICATIONS

Wolff Drugs & Gift, Zanfel package details.*
Q & A inset found in package, Experts Rave about Zanfel.*

* cited by examiner

*Primary Examiner* — Jean P Cornet
(74) *Attorney, Agent, or Firm* — King & Partners, PLC

(57) ABSTRACT

A solution for urushiol induced contact dermatitis is provided for in a topical solution. According to the invention, a method is provided for applying a composition of substances to the affected area, working the composition into the affected area, and removing the composition from the affected area. The composition comprises at least one ethoxylate in combination with a supporting agent. It is believed that this combination binds to the available urushiol receptors rendering it inactive. The affinity of the receptors for the ethoxylates also appears to cause a release of the urushiol from its epidermal bonds for bonding to the composition. An inert scrubbing agent, such as polyethylene beads, can also be included to assist in the release of the urushiol. Acetylated lanolin alcohol, EDTA, a foam stabilizer, and water can also be added to the composition without effecting performance.

1 Claim, No Drawings

METHOD FOR TREATING URUSHIOL INDUCED CONTACT DERMATITIS

I. RELATED APPLICATION

This application is a continuation of application Ser. No. 10/200,691, filed Jul. 22, 2002, now U.S. Pat. No. 7,008,963, which is a continuation-in-part of application Ser. No. 09/347,714, filed Jul. 3, 1999, now U.S. Pat. No. 6,423,746.

II. FIELD OF THE INVENTION

The present invention relates to solutions for allergic dermatitis and more particularly to a solution for *Toxicodendron* dermatitis, which results from contact with the Rhus oleoresin, urushiol.

II. BACKGROUND OF THE INVENTION AND PRIOR ART

Urushiol is the toxin responsible for the dermatitis caused by contact with the sap of commonly encountered noxious plants such as poison ivy (*T. rydbergii* (Northern and Western poison ivy) and *T. radicans* ssp. *radicans* (Eastern poison ivy)), poison oak (*T. toxicarium* (Eastern poison oak) and *T. diversilobum* (Western poison oak)), poison sumac (*T. verix*), and related plants found throughout the world. These plants are in the Anacardiaceae group, which also includes, among others, the lacquer tree of Asia, the mango tree, cashew shell oil, and certain nutshells, such as the walnut. (Throughout this document, reference to poison ivy is meant to also include other urushiol containing plants.)

When located inside an unruptured plant, urushiol is a light, colorless oil. When exposed to oxygen, urushiol easily oxidizes and, after polymerizing, turns a blackish color. The slightest contact or even breeze easily damages the leaves. Therefore, it is rare to find a plant that does not have at least some ruptured leaves. Most people believe that poison ivy infection can only result from contact with the leaves of the plant. This is not true. Urushiol is found not only in the leaves but also vines and stem and root systems. The urushiol in the root system and vines is pure and is ten to 100 times more potent than that found in leaves. Accordingly, contact with cut or broken vines, or root systems will almost always result in a reaction.

Experts estimate there are up to 55 million cases of urushiol-induced contact dermatitis annually in the United States. Roughly 85 percent of all people will develop an allergic reaction when adequately exposed to poison ivy. People who reach adulthood without becoming sensitive have only a 50 percent chance of developing an allergy to poison ivy. Sensitivity to poison ivy tends to decline after 72 years of age as the immune system is less reactive. Children under the age of 1 year do not typically react to urushiol as their immune systems are not yet fully developed.

The American Academy of Dermatology estimates that there are up to 50 million cases of urushiol induced contact dermatitis annually in the United States alone. No one is sure of the number of world wide annual exposures but some experts estimate that the number could be double that of the United States. Accordingly, urushiol induced contact dermatitis is a world wide problem.

Chemically, urushiols are mixtures of catechols with long, hydrophobic, carbon (alkyl) side chains at the three position of the catechol ring. For example, poison ivy contains predominantly 3-n-pentadececylcatechols (C-15) and poison oak contains predominantly 3-n-heptaecylcatechols (C-17).

Current theory suggests that the reaction to urushiol is a delayed cell-mediated immune response in which, upon first exposure, urushiol penetrates the stratified squamous epithelial cells and binds to the Langerhan cells, which, in turn, sensitize effector T-cells in the lymph system. Subsequent exposures to urushiol result in the release of cytokines and reaction by macrophages and cytotoxic T-Cells. The result of lytic enzyme and perform release is destruction of the membrane-bound urushiol and surrounding skin cells, which presents as the commonly seen clinical picture.

Once urushiol touches the skin, it begins to penetrate in minutes. It is completely bound to the skin after eight hours (two to six hours according to some experts). The rash generally develops within two days. Redness and swelling occur, often followed by blisters and severe itching. In a few days, the blisters may become crusted and begin to scale. The rash generally peaks after five days, and starts to decline after about a week or 10 days. The rash takes two or more weeks to heal. In a severe case or in a systemic reaction, individuals will many times present with black spots in areas of heavy urushiol concentration. The black spots are polymerized urushiol in a pure form and need to be removed immediately. This "Black Spot" test (attributed to Guin) is good indicator of a severe reaction, localized or systemic, or is often seen in cases of poison oak (typically a more tenacious reaction than poison ivy).

The rash can affect almost any part of the body, especially where the skin is thin, such as on the face. A rash develops rarely on the soles of feet and palms of hands, where the skin is thicker. The rash does not spread, although it may seem to do so when it breaks out in new areas. This may happen because urushiol absorbs more slowly into skin that is thicker, such as on forearms, legs and the body's trunk. Urushiol can be transferred by fingernails or animal fur and can remain on clothing, shoes, and tools for up to five years in moist climates and nine years in dry climates. Scratching the rash does not spread the urushiol to other parts of the body, but it can prolong the discomfort and cause a secondary infection.

Solution has historically consisted of attempting to remove the oil as quickly after exposure as possible: applying rubbing alcohol, washing affected areas with water, and showering with soap and water. In many instances, however, people either fail to fully remove the toxin before it has bound to the skin or don't realize they have been exposed until after the rash appears.

Over-the-counter solutions are legion; a partial list of the most popular includes hydrocortisone creams and ointments, diphenhydramine gels, calamine lotion, and the proprietary product, Ivy Dry®*. Hydrocortisone, diphenhydramine, and calamine lotion are palliatives and offer only temporary relief from the itching associated with *Toxicodendron* contact dermatitis. They do nothing to remove urushiol from the skin. Likewise, Ivy Dry® provides essentially a cooling effect that is only temporary. It may, if used before the urushiol binds to the skin, remove some of the urushiol.

Attempts have been made to find both prophylactic solutions as well as post-exposure solutions. To date, no vaccine has been developed and the prior art solutions are not without shortcomings. One solution example is seen in U.S. Pat. No. 5,686,074 to Stewart which teaches and claims a solution for poison ivy which includes a composition including linseed oil, an astringent, a starch, an essential oil and a citrus oil. One shortcoming of this patent is that linseed oil can cause irritation itself. A second shortcoming of this patent is that it requires that the composition be applied to the affected areas up to twice a day until the rash is gone. The composition provides what appears to be only very temporary palliative relief of poison ivy symptoms and does not appear to alter the course of the malady.

Other proposed solutions are seen in U.S. Pat. Nos. 5,620,527, 5,011,689, 4,499,086, 4,259,318, 4,002,737, 3,862,331, 3,875,301, and 3,922,342.

Yet other prior art attempts have focused on prophylactics for preventing the dermatitis. One example is seen is U.S. Pat. No. 4,663,151 to Waali that discloses and claims a prophylactic solution based upon Aluminum Chlorhydrate. Of course, the most significant shortcoming associated with prophylactic solutions is that they are only effective if applied before exposure to the urushiol; an occurrence that rarely takes place.

Tec Laboratories, Inc. of Albany, Oreg. markets an unpatented product sold under the mark Tech-Nu. This product also is not without shortcomings. This product was originally developed as a solution for radiation exposure. It was discovered, however, that the product also provided some relief for poison ivy exposure. The main active ingredient in the Tech-Nu® product is Octylphenoxy-polyethoxy-ethanol. The four octyl groups of this chemical are too large too surround the non polar moieties in the urushiol. Therefore, it only partially matches the polarity of urushiol. Thus, the action of this product renders the urushiol only partially inactive. Since the urushiol remains partially active and continues to cause irritation, only temporary relief is provided and multiple applications are necessary. Also, the chemical makeup of the product requires that it be applied no later than eight hours after exposure to urushiol.

There is need, therefore, for a safe, effective solution for dermatitis caused by exposure to the toxin urushiol. The solution should provide complete relief from the signs and symptoms associated with the dermatitis in limited solutions and be effective at any point during the dermatitis cycle.

II. OBJECTS OF THE INVENTION

It is an object of the present invention to provide a solution for urushiol induced allergic dermatitis (*Toxicodendron* dermatitis), the solution providing almost immediate and permanent relief in usually one solution.

It is a further object of the present invention to provide such a solution that utilizes a composition that chemically attaches to available urushiol receptors to block its allergic reaction properties and to release the urushiol so that it can be removed from the skin.

It is a yet further object of the present invention to provide a solution that is safe to use.

It is yet another object of the present invention to provide a solution for urushiol induced allergic dermatitis that is topical can be purchased over the counter and is economical.

IV. SUMMARY OF THE INVENTION

The above objects of the invention are provided for in a topical solution for use in urushiol induced contact dermatitis. According to the invention, a composition of substances is applied to and worked into the affected area. The solution is permitted to stay on the affected area a sufficient amount of time such that the solution has bonded with the urushiol, and the solution-urushiol complex is removed from the affected area. A secondary effect of the solution is that it interacts with the C fibers of the nervous system to provide itch relief.

The composition comprises at least one ethoxylate in combination with a compatible wetting agent, for non-limiting example, Sodium Lauroyl Sarcosinate (or SLS). It is believed that this combination creates an urushiol-complimentary polar substance that binds with available urushiol receptors rendering it inactive. The affinity of the receptors for the ethoxylates also appears to cause a release of the urushiol from its epidermal bonds creating a micelle with the inventive solution. An inert scrubbing agent, such as polyethylene beads or pumice, can also be included to assist in the release of the urushiol. Acetylated lanolin alcohol, EDTA, a foam stabilizer, water and other various agents can also be added to the composition without effecting performance.

V. DETAILED DESCRIPTION OF THE INVENTION

As noted above, urushiol is the toxin responsible for the contact dermatitis caused by poison ivy, poison oak, and other urushiol containing plants. When housed inside an unruptured plant leaf, urushiol is a light, colorless oil. The slightest contact or even breeze easily damages the leaves. Therefore, it is rare to find a plant that does not have at least some ruptured leaves. When exposed to oxygen, urushiol easily oxidizes and, after polymerizing, turns a blackish color.

The reaction experienced by most people is the result of exposure to the oleoresin containing the urushiol. The reaction is an allergic eczematous contact dermatitis characterized by redness, swelling, papules, vesicles, bullae, and streaking. Urushiol is the name given to a family catechols having long, hydrophobic, carbon (alkyl) side chains at the three position of the catechol ring. The urushiol of the poison ivy plant contains predominantly 3-n-pentadececylcatechols (C-15). Poison oak is known to contain predominantly 3-n-heptaecylcatechols (C-17). Other urushiol containing plants contain catechols that have side chains of varying lengths.

The inventor discovered that a hand scrub product manufactured and sold by the Redman Scientific, Company of Dallas, Tex. can alleviate the signs and symptoms of urushiol induced contact dermatitis. The product has been sold for approximately twenty years, and is known to be a safe, gentle hypoallergenic product. The product has been sold as an industrial hand cleaner and has never heretofore been known to be effective against urushiol toxicity. It has only been promoted as a hand cleaner.

Chemical analysis and research has revealed that two of the component parts of the Redman product are central to its effectiveness as a solution for urushiol induced contact dermatitis: an ethoxylate and Sodium Lauroyl Sarcosinate. The ethoxylate is a nonylphenol ethoxylate. The present invention's ethoxylate has the large octyl groups removed. In this way, the ethoxylate can "wrap" around the non-polar molecules of the urushiol. Further, the long chain moiety of the present invention's ethoxylate is only four carbons long, as opposed to, for example, that seen in Tec-Nu®. This feature also assists the ethoxylate in bonding to the urushiol more effectively. (It is important to note that more than one surfactant can be used at a time. Accordingly, the ethoxylate may be used alone or in conjunction with other surfactants to create the appropriate environment.)

However, the ethoxylate itself is not capable of forming a complete micelle with the urushiol. It was discovered that the addition of Sodium Lauroyl Sarcosinate completes a micelle and the urushiol can be cleansed away from the skin. SLS also has a long carbon chain that can surround the non-polar portions of the urushiol. In addition, SLS contains a highly polar end that aids in surrounding the polar ends of urushiol and also in the invention's reactivity with water.

Thus, the combination of the ethoxylate and SLS create a large molecule that contains flexible non-polar groups and soluble polar groups. This permits the inventive composition to quickly and effectively surround the urushiol and then be rinsed away with water, a highly polar substance.

Further research by the Inventor has revealed that other substances ("hereinafter termed "supporting agents") also are effective in combination with ethoxylates to bind and neutralize urushiol. For example, d-limonene can be used in combination with an ethoxylate to create an effective urushiol binding or neutralizing agent. The chemical result of the ethoxylate/d-limonene combination has an affinity to urushiol that is close but not the same as SLS; thus, d-limonene can be a suitable, but somewhat less effective, substitute for SLS. Further, d-limonene is known to be a mild skin irritant and may cause undue irritation of already disrupted skin.

Other substances that form with the ethoxylate to form a molecule that can create a micelle with the urushiol can also work as supporting agents.

Inert scrubbing agents improve the action of the inventive composition. The scrubbing agent assists by causing the urushiol to detach from the skin and place it in position for bonding with the active chemical components of the inventive composition. Any inert agent will suffice but the inventor believes that polyethylene beads work best. Another suitable inert agent includes pumice. The scrubbing agent should be large enough to be effective but not so large as to cause abrasions. Scrubbing agents should be in the range of 5 to 50 microns with an average size being approximately 25 microns or 50 mesh. While scrubbing agents are desirable, they are not critical to the invention use.

To make the inventive composition, an exact ratio of ethoxylate and supporting agent is not critical. The only requirement is that the ethoxylate completely reacts with the supporting agent, creating a polymer. This will vary with the ethoxylate and supporting agent used, but, in the case of SLS, a ratio of ethoxylate-to-SLS of 1.5:2 is preferred. The amount by weight of scrubbing agent can vary according to the grittiness desired. In the case of SLS and polyethylene beads, a formula of ethoxylate:SLS:polyethylene of 40:20:40 is preferred but that formulas of other concentrations are useful. Thus, for production purposes, formulas having a supporting agent ranging from 10 to 20% by weight, ethoxylate ranging from 20 to 40% by weight, and scrubbing agent from 20 to 50% by weight are reasonable. But again, the formula is not restricted to these ranges, which ranges are presented for example purposes only.

Also, a cutting agent that does not chemically react with the composition may be added but is not required. The cutting agent makes the overall composition flow more easily, thereby enabling more packaging options such as tubes. The cutting agent can be either an aqueous based solution or an oil based solution. The cutting agent must be added only in sufficient amount that it promotes flow but does not effect the action of the composition.

Thus, a representative composition for the inventive solution might be polyethylene granules, sodium lauroyl sarcosinate, nonoxynol-9, C12-15 pareth-9, disodium EDTA, quaternium-15, carbomer 2%, triethanolamine, and water.

In use, the composition is applied to an affected area and worked over the area by a scrubbing motion. After sufficient time has elapsed to ensure that the affected area has been adequately exposed to the composition, typically thirty seconds to three minutes depending on the agents used, severity of the reaction, and the sensitivity of the individual, the composition and bound urushiol are washed away. To have the greatest effect, the composition can be left on the affected area, after the initial scrubbing, for a short time, thirty to sixty seconds, a second rubbing can be accomplished. The second rubbing period can be shorter than the initial period and than washed away. Experiments have demonstrated that a majority of people needs only one solution to be relieved of itching; however, severe or systemic cases may require two or more application approximately eight hours apart for two days to be fully effective. The inventive composition works at varying rates of effectiveness at any time during the rash cycle.

I claim:

1. A method for treating urushiol induced contact dermatitis, consisting of the steps of:
    applying an aqueous topical composition to an area affected by urushiol induced contact dermatitis, wherein the topical composition consists of:
        water;
        an ethoxylate present in a concentration ranging from 20 percent to 40 percent by weight;
        d-limonene present in a concentration ranging from 10 percent to 20 percent by weight, and wherein the weight ratio of the ethoxylate to d-limonene is 1.5:2;
        polyethylene beads present in a concentration ranging from 20 percent to 50 percent by weight, and wherein the polyethylene beads range particle size from 5 microns to 50 microns;
        acetylated lanolin alcohol;
        ethylenediaminetetraacetic acid;
        C12-15 pareth-9;
        quaternium-15;
        carbomer; and
        triethanolamine; and
    removing the topical composition from the affected area after 30 seconds to three minutes.

* * * * *